United States Patent [19]

Mori et al.

[11] Patent Number: 5,254,471
[45] Date of Patent: Oct. 19, 1993

[54] CARRIER FOR CELL CULTURE

[75] Inventors: Yuuichi Mori, Shizuoka; Shigeyasu Kobayashi, Kanagawa; Miyoshi Okamoto, Osaka; Kouji Watanabe, Shiga; Shouji Nagaoka, Kanagawa, all of Japan

[73] Assignee: Toray Industries, Inc., Tokyo, Japan

[21] Appl. No.: 821,299

[22] Filed: Jan. 13, 1992

Related U.S. Application Data

[63] Continuation of Ser. No. 518,329, May 4, 1990, abandoned, which is a continuation of Ser. No. 221,244, Aug. 3, 1988, abandoned.

[30] Foreign Application Priority Data

Oct. 6, 1986 [JP]  Japan .................................. 61-236355

[51] Int. Cl.$^5$ ................................................. C12N 5/00
[52] U.S. Cl. .......................... 435/240.23; 435/240.2; 435/240.4; 435/180; 435/240.243
[58] Field of Search ................................. 435/177–182, 435/240.242, 285, 240.1, 240.2, 240.21, 240.23, 240.243, 240.4; 428/373

[56] References Cited

U.S. PATENT DOCUMENTS

| | | | |
|---|---|---|---|
| 3,418,200 | 12/1968 | Tanner | 428/373 |
| 3,516,239 | 6/1970 | Fukuda et al. | 428/373 X |
| 4,087,327 | 5/1978 | Feder et al. | 435/240.242 X |
| 4,189,534 | 2/1980 | Levine et al. | 435/70.3 |
| 4,368,227 | 1/1983 | Setsuie et al. | 428/91 |
| 4,610,962 | 9/1986 | Takagi et al. | 435/179 |
| 4,957,868 | 9/1990 | Yushina et al. | 435/177 X |
| 5,043,278 | 8/1991 | Nagaoka et al. | 436/181 |

FOREIGN PATENT DOCUMENTS 4822126 4/1973 Japan .
2178447 2/1987 United Kingdom .

Primary Examiner—James C. Housel
Assistant Examiner—Jeffrey R. Snay

[57] ABSTRACT

A carrier for cell culture comprising ultra fine fibers with a fineness of not more than 1.0 denier. The carrier makes it possible for the cells to retain their differentiation and proliferation ability for a long time. It also enables a large scale culturing.

12 Claims, No Drawings

CARRIER FOR CELL CULTURE

This application is a continuation of application Ser. No. 07/518,329 filed on May 4, 1990, now abandoned, which is a continuation of application Ser. No. 07/221,244, filed on Aug. 3, 1988, as PCT Application No. PCT/JP87/00740, now abandoned.

TECHNICAL FIELD

This invention relates to a carrier for culturing cells comprising ultra fine fibers, which is useful for culturing animal and plant cells.

BACKGROUND ART

Cell culturing methods are grouped into 1) monolayer culture, 2) suspension culturing and 3) embed culturing, depending on the carrier employed. In the monolayer culturing, the cells adhere, extend and proliferate on a culture plate made of glass, plastics or the like. In general, cells can proliferate only when they adhere to a carrier, so that the monolayer culturing is the most widely employed culturing method at present. On the other hand, in the case of culturing cells which do not necessitate the adhesion to a carrier, suspension culturing is generally employed wherein cells are cultured in suspended state in a culture medium. From the viewpoint of the efficiency of the culture, suspension culturing is most suitable. For adhesion-dependent cells, microcarrier culturing has been proposed, which is inbetween the monolayer culturing and the suspension culturing. However, it has been found that some kinds of cells, particularly most of the epithelial cells, cannot express their differentiation and proliferation functions in the monolayer culturing and the microcarrier culturing. Thus, a culturing method by which the differentiation and proliferation functions can be expressed is intensively studied.

It is considered that the cells normally differentiate and proliferate in the body because the microenvironment of the cells are suitable for the cells. More particularly, the facts that 1) the capillary system is streched around the cells and the feeding of nutrients to, and removal of wastes from the cells are efficiently effected in vivo, 2) different kinds of cells coexist and they interact with each other in vivo, and 3) cells exist in the mesenchyme consisting mainly of collagen fibers in vivo, so that they exist in a three-dimensional state, efficiently control the differentiation and proliferation of the cells. Application of the enviroment similar to that in the body to a culturing system is studied. For example, as a simulation of the capillary system controlling the feeding of nutrients and removal of wastes in vivo, a culturing system in which cells are cultured on the membranes of hollow fibers, and in which the feeding of nutrients and the removal of the wastes are conducted through the membranes of the hollow fibers, has been proposed and culturing with higher density than the conventional monolayer culturing has been accomplished. However, this culturing which employs the hollow fibers is a kind of the monolayer culturing. On the other hand, as a simulation of the mesenchyme, three-dimensional cell culture (embedded culturing) in collagen sponge or in collagen gel is intensively studiedrecently. By employing the collagen gel culturing method, differentiation and proliferation of the corpus mammae epithelium cells, hepatic parenchyma cells, salivary gland cells, thymus cells and pancreas cells, which have difficulties in expression of their differentiation and proliferation functions by the conventional monolayer culturing were first accomplished. In the conventional monolayer culturing, because the cells are cultured on the surface of the substrate, the cells have flat shapes which are utterly different from the normal morphology of the cells in vivo. In contrast, in the collagen gel culturing method, the morphology of the cells resembles that of the cells in vivo. On the other hand, while the cell proliferation is stopped upon complete covering of the surface by the cells in the monolayer culturing wherein the cells proliferate on the surface of the substrate, in the collagen gel culturing (three-dimensional culturing), the cells can consistently grow without changing the morphology. Thus, the embedded culturing represented by the collagen gel culturing provides an environment which is similar to the microenvironment in vivo. As a result, the environment suitable for expression of the differentiation and proliferation functions of the cells seems to be provided.

The above-mentioned facts indicate that the two elements, i.e., formation of the nutrients-feeding and wastes-removing route and the formation of the three-dimensional cell culturing carrier, are very important for the cell differentiation.

Although the differentiation and the proliferation of the cells which were difficult in the conventional monolayer culturing have been successfully attained by the three-dimensional culturing using the collagen gel, this culturing method has problems in that the mechanical strength of the collagen gel is small and the collagen gel is difficult to shape into various forms. These are big problems when, for examples, the culturing method is applied to a large scale culturing.

The object of the present invention is to provide a carrier for cell culture which satisfies the above-mentioned two elements and which also overcomes the above-mentioned problems in the collagen gel culturing.

DISCLOSURE OF THE INVENTION

The object has been accomplished by using ultra fine fibers. That is, this invention provides a carrier for cell culture comprising ultra fine fibers with a fineness of not more than 1.0 denier.

BEST MODE FOR CARRYING OUT THE INVENTION

The ultra fine fibers employed in the present invention has a fineness of not more than 1.0 denier, preferably not more than 0.5 denier.

The polymer constituting the ultra fine fibers may appropriately be selected from polyesters, polyamides, polytetrafluoroethylenes, polyolefins, cellulose, polyamino acids, collagen and the like, and polyesters are especially preferred.

Such polymers may have a substituent group with positive charge, such as diethylaminoethyl group.

In cases where fibers composed of a plurality of components are used, the component to remain may be selected from the above-mentioned polymers, and other components to be combined with the component to remain may appropriately be selected from polystyrenes, polyethylenes, water-soluble polyamides, polyesters soluble in aqueous alkaline solution, water-soluble polyvinyl alcohols and the like. The combination of the polymers may be chosen appropriately case by case depending on the spinning properties, processability, performance and the like.

Although the carrier for cell culture of the present invention may utilize the ultra fine fibers per se which are made of the above-mentioned polymers, in general, it is preferred that the fibers be in the form of a texture such as woven fabric, knit, non-woven fabric, spun yarn and cotton.

In forming the texture, the fibers which have already been in the form of the ultra fine fibers may be employed as they are. Alternatively, a texture may be first formed from fibers which can be made into ultra fine fibers by chemical or physical means, and the fibers are then made into ultra fine fibers to obtain a texture composed of ultra fine fibers. Ultra fine fibers may be obtained by carefully spinning a yarn by a conventional method. Alternatively, in case of employing polyesters, non-stretched fibers may be stretched in certain conditions into ultra fine fibers.

On the other hand, as fibers which can be made into ultra fine fibers in a later step, those multi-component fibers such as disclosed in Japanese Patent Publication (Kokoku) Nos. 22126/73 and 22593/78, which can be made into fibrils or ultra fine fibers by removing or peeling off a component of the multi-component fibers may be employed. With these fibers, since the fibers can be made into ultra fine fibers after processing and so the processing may be conducted when the fibers have an ordinary fineness, troubles in processing, such as breakage of fibers and generation of down during various fiber-processing steps in weaving or knitting may be minimized, thus it is preferred. The intervals among the fibers may preferably be several tens of micrometers, at least 10 micrometers.

The above-described texture made of the ultra fine fibers have a sufficiently high mechanical strength comparable to ordinary woven fabric or knit, and may be made into any form. For example, it can be formed into arbitrary forms such as film, rod, sphere (such as an aegagropila), flat rectangle, bellow and spiral, which greatly contributes to the promotion of efficiency and uniformity of the culture. The texture in the form of an aegagropila is especially preferred. The carrier thus formed may also be applied to pseudo suspension culturing using microcarriers.

Preferred results may usually be obtained by napping the texture made of the ultra fine fibers.

The napped texture herein means those having loop-naps and/or raised-naps, and the like. Non-limiting representative examples of the methods of napping the texture include a method in which loops are formed at the time of weaving or knitting, as in the case of manufacturing of cutting piles; a method in which the texture, after being formed, is processed by, for example, using a nap-raising machine to raise naps or by using a sharling machine; and, in some cases, buffing method using a sand paper.

By napping the texture made of ultra fine fibers, increase in the contact area of the cells, promotion of the softness of the texture which makes it possible to follow the morphological change of the cells, and promotion of porosity controlling the supply of nutrients and removal of wastes, are brought about, so that the performance as a carrier for cell culture is promoted.

The texture made of ultra fine fibers may be impregnated with collagen gel. By combining the texture with the collagen, the problems of the conventional collagen gel, i.e., its low mechanical strength and the difficulty in shaping, may be overcome.

The carrier of the present invention may be used for culturing various animal and plant cells. Although the cells to be cultured are not restricted, the carrier is especially suited for culturing adhesion-dependent cells. Specific examples of cells to be cultured include endothelial and epithelial cells such as vascular endothelial cells, smooth muscle cells, hepatic parenchyma cells, pancreas $\beta$ cells, epithelium cells and intestine cells; fibroblasts; and other organ parenchyma cells.

The cells may be cultured by conventional culturing methods using the carrier of the present invention.

The most characteristic feature of the carrier of the present invention is that the carrier for cell culture is made of ultra fine fibers. Surprisingly, it was found that the differentiation and proliferation functions of the cells are retained for a long period in the carrier made of the ultra fine fibers. Although the mechanism of this phenomenon has not yet been clearly understood, it is assumed as follows: As stated above, most of the cells are adhesion-dependent and can only grow when they adhere to a surface. Therefore, the most important property required for the carrier for cell culture is to provide sufficient scaffolding area which the cells can contact. The surface area (which the cells can contact) per unit volume of the texture made of ultra fine fibers is much larger than that of a texture made of fibers with ordinary fineness, thus providing a suitable environment for the adhesion-dependent cells.

On the other hand, in the texture of woven fabric, knit or non-woven fabric, the surface of the fibers form three-dimensional space so as to provide a morphology similar to that of the mesenchyme consisting chiefly of collagen fibers. As stated above, most of the epithelium cells can express their differentiation and proliferation functions as in vivo only when they are cultured by the three-dimensional culturing method using collagen gel. It is said that this is because the morphological change of the cells in the three-dimensional culturing is smaller than that shown in the two-dimensional culturing (monolayer culturing), and the cells have very similar morphology to that of the cells in vivo. Further, while the proliferation in the two-dimensional culturing is limited because the proliferation is effected in a plane, in three-dimensional culturing, the proliferation is not stopped because the three-dimensional space is utilized. This is also an important point. In particular, the three-dimensional space provided by the ultra fine fibers is more flexible than that provided by fibers with ordinary fineness, so that it can follow the morphological change of the cells. As a result, it can allow the cells to employ more physiological morphology. As mentioned above, it is presumed that the cell culture utilizing the flexible texture (three-dimensional space) provided by the ultra fine fibers would give the cells more comfortable environment.

On the other hand, as to another important element for the cultured cells, i.e., supply of nutrients and removal of wastes, by employing the ultra fine fibers, the porosity which controls the supply of nutrients and the removal of wastes, as well as the uniformity thereof is promoted. Therefore, in a cell culture in the texture made of ultra fine fibers, the ingestion of nutrients from, and excretion of wastes to the external environment are much easier than in the case of employing a texture made of fibers with ordinary fineness. Further, this property is much better than that provided by the conventional collagen gel. This is because that the diffusion speed of substances, especially the diffusion speed of the medium to large molecular substances in the structure of the present invention is much greater than that in the collagen gel. Thus, from the viewpoint of nutrients supply and wastes removal, the texture made of ultra fine fibers, again, provides the cultured cells with suitable environment.

Further, since the carrier for cell culture, which is made of ultra fine fibers has a great mechanical strength and is easy to make into various forms, it is possible to employ the carrier in large scale culturing.

The present invention will now be described concretely by way of examples.

EXAMPLE 1

A woven fabric was prepared using composite fibers 150D-42f (with a single yarn fineness of about 0.1 denier) defined in Japanese Patent Publication (Kokoku) No. 22126/73, which fibers contained 50 parts of island component polyester and 50 parts of sea component polystyrene and which contained 16 islands. After shrinkage, the fabric was immersed in trichloroethylene to remove polystyrene and dried.

After sterilization with an autoclave, the fabric was placed on a petri dish and 10 ml of human fibroblasts (with a cell population of $1 \times 10^5$ cells/ml) was injected into the fabric. The cultivation was conducted in a carbon dioxide gas incubator at 37° C. for 4 days. The cell density at day 4 was $1.6 \times 10^7$ cells/25 cm$^2$/10 ml. As a control, similar experiment was conducted using a plastic petri dish to obtain a final cell density of about $5 \times 10^6$ cells/25 cm$^2$/10 ml. Thus, it was proved that the cell density of the cultured cells is greatly promoted when the culture substrate of the present invention is used.

EXAMPLE 2

The fabric obtained in Example 1 was placed on a plastic petri dish and rat hepatic cells were injected therein at a cell population of about $5 \times 10^4$ cells/ml. The culture medium was RPMI 1640 (containing 10% of FCS). The cultivation was conducted in a carbon dioxide gas incubator. After 6 days, the cell population was increased to about $3.2 \times 10^5$ cells/ml and the hepatic cells kept alive for more than 2 weeks. On the other hand, as a control, cultivation was conducted in the same manner except that a petri dish coated with the cell matrix was used. In the control experiment, most of the cells died in 6 days of cultivation. These results show that the life of the hepatic cells is greatly prolonged when the culture substrate of the present invention is used.

EXAMPLE 3 AND COMPARATIVE EXAMPLE

Naps were raised on the fabric obtained in Example 1 with an abrasive paper and the fibers were intermingled with a high pressure water flow. The fabric was then cut into circles with 1.5 cm diameter and the circles were placed in wells of a 24-well microplate. Then $5 \times 10^4$ smooth muscle cells obtained from the thoracic aorta of a rabbit were suspended in 1.5 ml of culture medium and the suspension was added to the fabric. The culture medium was Dulbecco's modified Eagle MEM medium containing 20% of fetal calf serum, and the cultivation was conducted by gently shaking the microplate in a $CO_2$ incubator at 37° C. for 7 days. After the cultivation, all cells were detached by treating the cells with 0.005% trypsin in PBS at 37° C. for 10 minutes and the number of the cells were counted using a hemacytometer. The cell number was $4.0 \times 10^5$.

The cell number of the cells cultivated on a similar napped fabric made of fibers with a fineness of 1.4 denier in a comparative example was $0.8 \times 10^5$, and the cell number of the cells cultivated on a microplate with the same area was $0.2 \times 10^5$.

INDUSTRIAL APPLICABILITY

Since the carrier for cell culture of the present invention has great flexibility so as to sufficiently follow the morphological change of the cells, the compatibility thereof with the cells is high. Therefore, it can allow the cells to retain their differentiation and proliferation ability for a long period of time. Further, as it has a high mechanical strength and is easy to shape, it is useful as a carrier for large scale culturing.

We claim:

1. In a method for culturing animal and plant cells in which the cells differentiate and proliferate on a carrier, the improvement which comprises producing, as a carrier for the cell culture, a composite of ultra fine fibers having a fineness of less than 0.5 denier.

2. The method of claim 1, wherein the ultra fine fibers are formed into configurations selected from the group consisting of films, rods, spheres, flat rectangles, bellows, and spirals.

3. The method of claim 1, wherein the ultra fine fibers are in the form of a texture which is impregnated with a collagen gel.

4. The method of claim 1, wherein the cells to be cultured are endothelial or epithelial cells selected from the group consisting of vascular endothelial cells, smooth muscle cells, hepatic parenchyma cells, pancreas $\beta$ cells, epithelium cells, intestine cells, fibroblasts and other parenchyma cells.

5. The method of claim 1, wherein the ultra fine fibers are made of one or more polymers selected from the group consisting of polyesters, polyamides, polyolefins, cellulose, polyamino acids, and collagen.

6. The method of claim 5, wherein one of said polymers contains a diethylaminoethyl group with a positive charge.

7. The method of claim 5, wherein additional fiber components are combined therewith, said additional fibers being made from polymers selected from the group consisting of polystyrenes, polyethylenes, water soluble polyamides, polyesters soluble in aqueous alkaline solutions, and water-soluble polyvinyl alcohols.

8. The method of claim 1, wherein said fibers are in the form of a textured woven or non-woven fabric, knit, or spun yarn.

9. The method of claim 8, wherein the interval between the fibers is at least ten micrometers.

10. The method of claim 8, wherein the ultra fine fibers are napped to increase the surface contact area.

11. The method of claim 1, wherein said fibers are made by removing a component from multi-component fibers.

12. The method of claim 11, wherein said fibers are polyester.

* * * * *